(12) United States Patent
Zhao et al.

(10) Patent No.: US 10,987,338 B2
(45) Date of Patent: *Apr. 27, 2021

(54) COMPOSITION CONTAINING ARTESUNATE

(71) Applicants: Ming Zhao, Darien, IL (US); Li-Ming Zhou, Darien, IL (US)

(72) Inventors: Ming Zhao, Darien, IL (US); Li-Ming Zhou, Darien, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/572,558

(22) Filed: Sep. 16, 2019

(65) Prior Publication Data

US 2020/0022950 A1 Jan. 23, 2020

Related U.S. Application Data

(63) Continuation of application No. 16/068,365, filed as application No. PCT/US2017/013576 on Jan. 13, 2017, now Pat. No. 10,471,042.

(60) Provisional application No. 62/279,368, filed on Jan. 15, 2016.

(30) Foreign Application Priority Data

Apr. 19, 2016 (CN) .......................... 201610243279.5

(51) Int. Cl.
| | | |
|---|---|---|
| A61K 31/357 | (2006.01) | |
| A61K 31/133 | (2006.01) | |
| A61K 9/08 | (2006.01) | |
| A61K 47/18 | (2017.01) | |
| A61K 47/12 | (2006.01) | |
| A61K 47/24 | (2006.01) | |
| A61K 45/06 | (2006.01) | |
| A61K 9/00 | (2006.01) | |
| A61K 47/22 | (2006.01) | |
| A61K 47/26 | (2006.01) | |

(52) U.S. Cl.
CPC .......... *A61K 31/357* (2013.01); *A61K 9/0019* (2013.01); *A61K 9/08* (2013.01); *A61K 31/133* (2013.01); *A61K 45/06* (2013.01); *A61K 47/12* (2013.01); *A61K 47/18* (2013.01); *A61K 47/22* (2013.01); *A61K 47/24* (2013.01); *A61K 47/26* (2013.01); *Y02A 50/30* (2018.01)

(58) Field of Classification Search
CPC .... A61K 31/133; A61K 31/357; A61K 47/12; A61K 47/18; A61K 31/13; A61K 47/22; A61K 47/24; A61K 47/26; A61K 9/0019; A61K 9/08; A61K 45/06; A61P 19/00; A61P 19/02; A61P 19/04; A61P 1/00; A61P 1/02; A61P 1/16; A61P 1/18; A61P 25/00; A61P 29/00; A61P 31/00; A61P 31/02; A61P 31/04; A61P 31/06; A61P 31/10; A61P 31/12; A61P 35/00; A61P 35/02; A61P 37/08; A61P 3/10; A61P 41/00; A61P 43/00; A61P 9/00; A61P 9/04; A61P 9/10; Y02A 50/30
See application file for complete search history.

(56) References Cited

U.S. PATENT DOCUMENTS

| | | | |
|---|---|---|---|
| 3,718,664 A | 2/1973 | Riera et al. | |
| 4,675,315 A | 6/1987 | Prieto et al. | |
| 6,544,954 B1 * | 4/2003 | Hu ...................... | A61K 9/0019 |
| | | | 514/23 |
| 7,678,828 B2 | 3/2010 | Ellis et al. | |
| 9,603,831 B2 | 4/2017 | Thiemermann | |
| 9,623,005 B2 | 4/2017 | Thiemermann | |
| 2003/0171424 A1 | 9/2003 | Lin et al. | |
| 2013/0085159 A1 | 4/2013 | Boechat et al. | |
| 2014/0296532 A1 | 10/2014 | Chen et al. | |

FOREIGN PATENT DOCUMENTS

| | | |
|---|---|---|
| CN | 85100781 A1 | 8/1986 |
| CN | 101427997 A | 11/2007 |
| CN | 101623255 A | 1/2010 |
| CN | 103705475 A | 4/2014 |
| CN | 104414977 A | 3/2015 |
| CN | 105078964 A | 11/2015 |
| CN | 108309932 A | 7/2018 |
| WO | WO2011009956 A | 1/2011 |
| WO | WO2013108180 A | 7/2013 |

OTHER PUBLICATIONS

Efferth, T. et al. (Apr. 2001). "The Anti-malarial Artesunate is Also Active Against Cancer," Int. J. Oncol. 18(4):767-773.
Sun, L.H. et al. (Aug. 2007). "Effect of Artemisinin on Ischemia/Reperfusion Injury of Isolated Rat Myocardium," Zhongguo Zhong Yao Za Zhi, 32(15):1547-51.
Li, B. et al. (Mar. 2008). "Antimalarial Artesunate Protects Sepsis Model Mice Against Heat-Killed *Escherichia Coli* Challenge by Decreasing TLR4, TLR9 mRNA Expressions and Transcription Factor NF-Kappa B Activation," Int. Immunopharmacol. 8(3):379-389.
Agnihotri, J. et al. (Jan. 2013). "Formal Chemical Stability Analysis and Solubility Analysis of Artesunate and Hydroxychloroquinine for Development of Parenteral Dosage Form," J. Pharmacy Res. 6(1):117-122.
Ho, W.E. et al. (Apr. 2014). "Artemisinins: Pharmacological Actions Beyond Anti-Malarial," Pharmacol. Ther. 142(1):126-139.
Lai, L et al. (Oct. 2015). "Artesunate Alleviates Hepatic Fibrosis Induced by Multiple Pathogenic Factors and Inflammation Through the Inhibition of LPS/TLR4/NF-Kb Signaling Pathway in Rats," Eur. J. Pharmacol. 765:234-241.
Reid, B.G. et al. (Aug. 2016). "Discovery of novel small molecule inhibitors of cardiac hypertrophy using high throughput, high content imaging," J. Mol. Cell Cardiol. 97:106-113.
Li, J. et al. (Jan. 12, 2017). "Artemisinins Target GABAA Receptor Signaling and Impair α Cell Identity," Cell. 168(1-2):86-100.
Mikomangwa, W.P. et al. (Apr. 11, 2019). "Level of Knowledge Among Health Care Providers on Preparation of Injectable Artesunate for Treatment of Severe Malaria in Public Health Facilities in Tanzania," BMC Res. Notes. 12:224-228.
Guidelines for Administration of Injectable Artesunate for Severe Malaria, 2014, provided by the Medicines for Malaria Venture (MMV).

* cited by examiner

Primary Examiner — Sarah Pihonak

(57) ABSTRACT

The present disclosure provides a composition of artesunate, a process of preparing the same, and a method of treatment.

9 Claims, No Drawings

COMPOSITION CONTAINING ARTESUNATE

CROSS-REFERENCE TO RELATED APPLICATION AND INCORPORATION BY REFERENCE

The present application is a continuation application of U.S. patent application Ser. No. 16/068,365, filed Jul. 6, 2018, which is a U.S. National Phase filing of International Application No. PCT/US2017/013576, filed Jan. 13, 2017, which claims priority to U.S. Provisional Patent Application No. 62/279,368, filed Jan. 15, 2016, and Chinese Application No. 201610243279.5, filed Apr. 19, 2016, the entireties of which are hereby incorporated by reference.

FIELD

The present disclosure relates to a pharmaceutical composition containing artesunate, a process for the preparation of the composition, and a use of the composition as a medicament.

BACKGROUND

Artesunate is a derivative of artemisinin, the active antimalarial component isolated from herb *Artemisia annua* (qinghaosu) in 1972, and synthesized by reacting dihydroartemisinin with succinic acid anhydride in basic medium (CN 85100781). Artesunate is widely used for the treatment of malaria, especially effective in the treatment of sever and multiple drug-resistant malaria. More importantly, artesunate is the only artemisinin analogue that can be administered intravenously and the World Health Organization (WHO) guidelines recommend intravenous artesunate as first line therapy for severe malaria (World Health Organization, Guidelines for the treatment of malaria; Second edition 2010). Moreover, recent studies have shown that artesunate has broad biological activities beyond antimalaria, ranging from anticancer, antivirus, treatment of inflammatory and immune diseases, and other parasite-related infections (e.g. schistosoma japonicum and toxoplasma) to antifungals (Ho et al, Pharmacol Ther, 2014, 142(1):126-139).

Liu describes artesunate for use in the treatment of malaria (Artesunate Research and Development, Lijiang Press, Jul. 1, 2010, 3-20). Efferth et al. report anticancer activity of artesunate against 55 cancer cell lines of the Departmental Therapeutics Program of the National Institutes of Health and cancer cells resistant to doxorubicin, vincristine, methotrexate and hydroxyurea (Int J Oncol, 2001, 18, 767-773). Ho et al. publish a comprehensive review on artemisinins in diseases conditions beyond malaria, including cancer, viral, fungal infection, other parasite infections, and inflammatory disorders (Pharmacol Ther, 2014, 142, (1):126-39). Yu et al. describe the treatment of lupus with artesunate (Chinese J Derm, 1997, 30, 51-53).

Sun et al. describe effect of artemisinin on ischemia/reperfusion injury of isolated rat myocardium (Zhongguo Zhong Yao Za Zhi, 2007, 32, 15:1547-51). Zhang et al. describe the use of artesunate in combination with a chemotherapy regimen of vinorelbine and cisplatin to treat patients with advanced non-small cell lung cancers (J Chin Integr Med, 2008, 6(2):134). Li et al. report use of artesunate for the treatment of sepsis model mice against heat-killed *E. coli* challenges (Int Immnopharmacol, 2008, 8, 379-389). Liu et al. describe artesunate for use in the treatment of severe malaria and sepsis or organ damage induced by malaria infections (J Trop Med, 2009, 9(7) 755-756). WO2012168450 describes the ability of artesunate and its analogs to provide protection against organ injury caused by trauma haemorrhage and in stoke and burns injury, and to reduce the infarct size in myocardial infarction or to reduce the level of damage after the infarction has taken place. WO2014090306 describes artesunate for use in the treatment of acute, chronic kidney injury, uremia and in surgery that results in ischaemia-reperfusion (kidney transplantation, kidney and pancreas transplantation, coronary artery bypass graft).

Reid et al. describe the ability of artesunate to block left ventricular hypotrophy and improve cardiac function in adult mice subjected to transverse aortic constriction (J Mol Cell Cardiol, 2016, 97:106-13). Li et al. describe the use of artemisinin and its analogs to convert pancreatic a cells into β like cells through enhanced GABA signaling, restoring insulin production (Cell, 2017, 167, 1-15).

WO 2010/0137246 describes the use of artesunate in the treatment of asthma and respiratory distress syndrome. CN20151513816 describes artesunate for use in the treatment of idiopathic pulmonary fibrosis. Lai et al. describe the use of artesunate to alleviate hepatic fibrosis induced by multiple pathogenic factors (Eur J Pharmacol, 2015, 765, 234-241). All references described herein are incorporated by reference.

Artesunate is soluble in organic solvents, such as acetone and methanol, and slightly soluble in water. It becomes water soluble once formulated with 5% sodium bicarbonate solution and this formulation has been used in the clinic for more than 30 year as its only parenteral dosage form. Many studies have found that artesunate is unstable under basic and acidic conditions. It is also susceptible to degradation by moisture and heat (Agnihotri J. et al, J Pharmacy Res, 2013, 6:117-122). Therefore, artesunate injection has to be prepared immediately before use. The sodium bicarbonate formulation involves two-step preparation as instructed by the manufacturer (Guilin Pharmaceuticals, Guangxi, China). With a unit dosage of 60 mg, the first step is to dissolve artesunate by adding 0.6 mL or 1 mL of 5% sodium bicarbonate (2.3 equivalent or 3.8 equivalent, respectively) to artesunate powder and mixing vigorously for several minutes to have a clear solution, followed by the second step of dilution with 5.4 mL, or 5 mL, of 5% glucose or normal saline to the final concentration of 60 mg/6 mL. The dissolution produces significantly carbon dioxide bubbles upon the introduction of 5% sodium carbonate solution, reducing the contact of the drug powder with dissolution medium and thus lengthening the time needed for a complete dissolution. In addition, it is very difficult to determine whether artesunate is completely dissolved due to cloudiness caused by fizzing. This method is slow and complex. In this solution, artesunate starts to degrade within ten minutes and precipitation occurs within 2-3 hours (CN104414977). Therefore, a need exists for a new parenteral formulation, which should provide improved dissolution characteristics and enhanced stability of artesunate in aqueous solution.

SUMMARY

In the first aspect, a composition comprises artesunate and an organic base.

In the second aspect, a composition comprises artesunate and an organic base, wherein the organic base is a 5-8 membered ring compound, wherein each of the ring members is independently selected from carbon, nitrogen, oxygen, sulfur, and at least one ring member is nitrogen;

wherein the ring contains zero, one, two, or three double bonds; and wherein the ring is substituted by k substituents independently selected from $R^{1a}$, k is 0, 1, 2, 3, 4, 5, 6, 7, or 8; and two or more substituents $R^{1a}$ are selected independently from one another;

wherein $R^{1a}$ is selected from the group consisting of hydrogen, halogen, cyano, azido, nitro, SCN, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl; or $R^{1a}$ may combine with an atom or atoms to which it is attached to form unsubstituted or substituted $C_{3-12}$ cycloalkyl, unsubstituted or substituted 3- to 12- membered heterocyclic, unsubstituted or substituted $C_{6-12}$ aryl, or unsubstituted or substituted 5- to 12-membered heteroaryl.

In the third aspect, a process of preparing a composition comprises: providing artesunate; providing a solution comprising an organic base; and adding the solution to artesunate to provide the composition.

In the fourth aspect, the present disclosure provides a method for treatment.

DETAILED DESCRIPTION

Definitions

Any terms in the present application, unless specifically defined, will take the ordinary meanings as understood by a person of ordinary skill in the art.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group, such as benzyl, may be substituted as described in the definition of the term "aryl."

The term "alkoxy," as used herein, refers to a $C_1$-$C_{12}$, preferably $C_1$-$C_6$, alkyl group attached to the parent molecular moiety through an oxygen atom. Representative examples of alkoxy group include, but are not limited to, methoxy ($CH_3O$), ethoxy ($CH_3CH_2O$), and t butoxy (($CH_3$)$_3$CO).

The term "alkyl," as used herein, refers to a group derived from a straight or branched chain saturated hydrocarbon by removal of a hydrogen from one of the saturated carbons. The alkyl group preferably contains from one to ten carbon atoms, more preferably one to six carbon atoms. Representative examples of alkyl group include, but are not limited to, methyl, ethyl, isopropyl, and tert-butyl.

The term "aryl," as used herein, refers to a group derived from a $C_6$-$C_12$, preferably $C_6$-$C_{10}$, aromatic carbocycle by removal of a hydrogen atom from an aromatic ring. The aryl group can be monocyclic, bicyclic or polycyclic. Preferred examples of aryl groups include phenyl and naphthyl.

The term "cyano," as used herein, refers to CN.

The term "cycloalkyl," as used herein, refers to a group derived from a monocyclic saturated carbocycle, having preferably three to eight, more preferably three to six, carbon atoms, by removal of a hydrogen atom from the saturated carbocycle. Representative examples of cycloalkyl groups include, but are not limited to, cyclopropyl, cyclopentyl, and cyclohexyl. When a cycloalkyl group contains one or more double bond(s) in the ring, yet not aromatic, it forms a "cycloalkenyl" group.

The terms "halo" and "halogen," as used herein, refer to F, Cl, Br, or I.

The term "haloalkyl," as used herein, refers to a $C_1$-$C_{10}$, preferably $C_1$-$C_6$, more preferably $C_1$-$C_4$, alkyl group substituted by at least one halogen atom. The haloalkyl group can be an alkyl group of which all hydrogen atoms are substituted by halogens. Representative examples of haloalkyl include, but are not limited to, trifluoromethyl ($CF_3$), 1-chloroethyl ($ClCH_2CH_2$), and 2,2,2-trifluoroethyl ($CF_3CH_2$).

The term "hydroxylalkyl," as used herein, refers to alkyl group as defined above which is substituted with at least one hydroxy group.

The term "heteroaryl," as used herein, refers to a 5- to 10-membered, monocyclic or bicyclic aromatic group comprising one or more, preferably one to three, heteroatoms independently selected from nitrogen, oxygen, and sulfur in the aromatic ring(s). As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, pyrimidinyl, furyl, thienyl, isoxazolyl, thiazolyl, isoxazolyl, oxazolyl, indolyl, quinolinyl, isoquinolinyl, benzisoxazolyl, benzothiazolyl, and benzothienyl.

The term "heterocyclyl," as used herein, refers to a 3- to 10-membered monocyclic or bicyclic nonaromatic group comprising one or more, preferably one to three, heteroatoms independently selected from nitrogen, oxygen, and sulfur in the nonaromatic ring(s). The heterocyclyl groups of the present disclosure can be attached to the parent molecular moiety through a carbon atom or a nitrogen atom in the group. A heterocylcyl group can be saturated or unsaturated, for example, containing one or more double bond(s) in the ring. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl, or the like.

The terms "hydroxy" or "hydroxyl," as used herein, refers to OH.

The term "nitro," as used herein, refers to $NO_2$.

The term "substituted" as used herein, refers to independent replacement of one, two, or three or more of the hydrogen atoms thereon with substituents including, but not limited to, —F, —Cl, —Br, —I, —OH, protected hydroxy, —$NO_2$, —CN, —$NH_2$, $N_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH-alkyl, —NH-alkenyl, —NH-alkynyl, —NH-cycloalkyl, —NH-aryl, —NH-heteroaryl, —NH-heterocycloalkyl, -dialkylamino, -diarylamino, -diheteroarylamino, —O-alkyl, —O-alkenyl, —O-alkynyl, —O-cycloalkyl, —O-aryl, —O-heteroaryl, —O-heterocycloalkyl, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —NHCO$_2$-alkyl, —NHCO$_2$-alkenyl, —NHCO$_2$-alkynyl, —NHCO$_2$-cycloalkyl, —NHCO$_2$-aryl, —NHCO$_2$-heteroaryl, —NHCO$_2$-heterocycloalkyl, —NHC(O)NH$_2$, —NHC(O)NH-alkyl, —NHC(O)NH-alkenyl, —NHC(O)NH-alkynyl, —NHC(O)NH-cycloalkyl, —NHC(O)NH-aryl, —NHC(O)NH-heteroaryl, —NHC(O)NH-heterocycloalkyl, NHC(S)NH$_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)NH$_2$, —NHC(NH)NH-alkyl, —NHC(NH)NH-alkenyl, —NHC(NH)NH-alkynyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkynyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-SO$_2$NH$_2$, —SO$_2$NH-alkyl, —SO$_2$NH-alkenyl, —SO$_2$NH-alkynyl, —SO$_2$NH-cycloalkyl, —SO$_2$NH-aryl, —SO$_2$NH-heteroaryl, —SO$_2$NH-heterocycloalkyl, —NHSO$_2$-alkyl, —NHSO$_2$-alkenyl, —NHSO$_2$-alkynyl, —NHSO$_2$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, -cycloalkyl, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

When any group, for example, alkyl, alkenyl, "cycloalkyl," "aryl," "heterocyclyl," or "heteroaryl", is said to be "optionally substituted," unless specifically defined, it means that the group is or is not substituted by from one to five, preferably one to three, substituents independently selected from halogen, alkyl, alkoxy, haloalkyl, haloalkoxy, hydroxy, oxo, acyl, cyano, nitro, and amino group, or the like, provided that such substitution would not violate the conventional bonding principles known to a person of ordinary skill in the art. When the phrase "optionally substituted" is used before a list of groups, it means that each one of the groups listed may be optionally substituted.

The term "artesunate" as used in this specification encompasses any of the individual enantiomers of artesunate; the term may refer to just a single enantiomer, or a racemic or non-racemic mixture of the enantiomers. The term "artesunate" also includes polymorphs and hydrates of artesunate. The terms "artesunate" also includes salts and esters of artesunate. One example of the salt is the sodium salt. The term "artesunate" also includes prodrugs of artesunate, and enantiomers, racemic mixtures, non-racemic mixtures, polymorphs, hydrates, salts and esters of said prodrugs.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "buffering agent" as used herein denotes a pharmaceutically acceptable excipient, which stabilizes the pH of a pharmaceutical preparation. Suitable buffering agents are well known in the art and can be found in the literature. Preferred pharmaceutically acceptable buffering agents comprise but are not limited to histidine-buffers, glycine-buffers, citrate-buffers, succinate-buffers, acetate-buffers, ammonium-buffers, tris(hydroxymethyl)aminomethane-buffers (Tris), and phosphate-buffers. Preferred buffers comprise acetic acid, succinic acid (20-50 mM) and phosphoric acid (20-50 mM). Most preferred buffers comprise citrate, phosphate, L-histidine or mixtures of L-histidine and L-histidine hydrochloride. Other preferred buffers are acetate buffer, L-arginine buffer, L-lysine buffer and L-glycine buffer. Independently from the buffer used, the pH can be adjusted with an acid or a base known in the art, e.g. hydrochloric acid, acetic acid, phosphoric acid, sulfuric acid and citric acid, sodium hydroxide, sodium bicarbonate, potassium hydroxide, and potassium bicarbonate.

The term "subject" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Compositions

Composition I

In one embodiment, a composition comprises artesunate (scheme 1) and an organic base.

Scheme 1. Artesunate

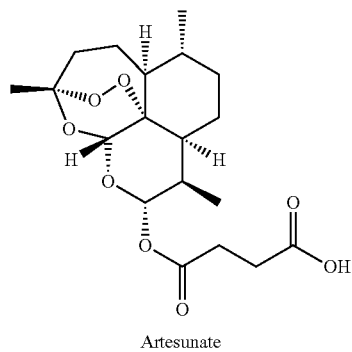

Artesunate

In some embodiments, the composition comprises artesunate and an organic base of formula (I):

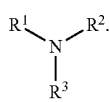

$R^1$, $R^2$ and $R^3$ are independently selected from the group consisting of absent, hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl; or $R^2$ and $R^3$ may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, $R^1$ is hydrogen. In some embodiments, $R^1$ and $R^2$ are hydrogen.

In some embodiments, at least one of $R^1$, $R^2$ and $R^3$ is $C_{1-6}$ alkyl substituted with a member selected from the group consisting of hydroxyl, thiol, carboxyl, carboxylate, carbamoyl, ester and amine.

In some embodiments, at least one of $R^1$, $R^2$ and $R^3$ is alkyl substituted with hydroxyl group. In some embodiments, two of $R^1$, $R^2$ and $R^3$ are alkyl substituted with hydroxyl group. In some embodiments, $R^1$, $R^2$ and $R^3$ are alkyl substituted with hydroxyl group. In some embodiments, at least one of $R^1$, $R^2$ and $R^3$ is hydroxyalkyl. In some embodiments, at least two of $R^1$, $R^2$ and $R^3$ are hydroxyalkyl. In some embodiments, at least one of $R^1$, $R^2$ and $R^3$ is $C_{1-6}$ hydroxyalkyl. In some embodiments, at least two of $R^1$, $R^2$ and $R^3$ are $C_{1-6}$ hydroxyalkyl. In some embodiments, $R^1$, $R^2$ and $R^3$ are $C_{1-6}$ hydroxyalkyl. In some embodiments, $R^2$ and $R^3$ are —$(CH_2)_q OH$, and q is an integer from 1 to 6. In one embodiment, q is 2. In some embodiments, q is 3. In some embodiments, $R^1$, $R^2$ and $R^3$ are —$(CH_2)_q OH$. In some embodiments, q is 2. In some embodiments, q is 3.

In some embodiments, at least one of $R^1$, $R^2$ and $R^3$ is alkyl substituted with carboxyl group. In some embodiments, two of $R^1$, $R^2$ and $R^3$ are alkyl substituted with carboxyl group. In some embodiments, $R^1$, $R^2$ and $R^3$ are alkyl substituted with carboxyl group. In some embodiments, at least one of $R^1$, $R^2$ and $R^3$ is alkyl substituted with carboxylate group. In some embodiments, two of $R^1$, $R^2$ and $R^3$ are alkyl substituted with carboxylate group. In some embodiments, $R^1$, $R^2$ and $R^3$ are alkyl substituted with carboxylate group. In some embodiments, $R^1$, $R^2$ and $R^3$ are independently —$(CH_2)_n COOM$. n is an integer from 1 to 6. In some embodiments, n is 1. M is a cation. In some embodiments, M is alkali metal, alkaline earth metal, or ammonium. In some embodiments, M is sodium. In some embodiments, M is potassium. In some embodiments, at least one of $R^1$, $R^2$ and $R^3$ is —$(CH_2)_n COONa$. In some embodiments, at least one of $R^1$, $R^2$ and $R^3$ is —$CH_2 COONa$.

In some embodiments, $R^1$, $R^2$ and $R^3$ are independently selected from the group consisting of hydrogen, tris(hydroxyalkyl)methyl, and —$(CH_2)_n COOH$.

In some embodiments, at least one of $R^1$, $R^2$ and $R^3$ is tris(hydroxyalkyl)alkyl. tris(hydroxylC$_{1-6}$alkyl) C$_{1-6}$alkyl. In some embodiments, $R^3$ is tris(hydroxyalkyl)alkyl. In some embodiments, $R^3$ is tris(hydroxylC$_{1-6}$alkyl) C$_{1-6}$alkyl. $R^1$ and $R^2$ are hydrogen. In some embodiments, $R^3$ is tris(hydroxylC$_{1-2}$alkyl) C$_{1-2}$alkyl. In some embodiments, $R^3$ is tris(hydroxymethyl)methyl. $R^1$ and $R^2$ are hydrogen.

In some embodiments, only one of $R^1$, $R^2$ and $R^3$ is tris(hydroxyalkyl)methyl. In some embodiments, $R^1$ and $R^2$ are hydrogen. In some embodiments, at least one of $R^1$, $R^2$ and $R^3$ is tris(hydroxyC$_{1-6}$alkyl)methyl. In some embodiments, at least one of $R^1$, $R^2$ and $R^3$ is tris(hydroxyC$_{1-2}$alkyl)methyl.

In some embodiments, $R^3$ is tris(hydroxyC$_{1-6}$alkyl)methyl, and $R^1$ and $R^2$ are hydroxylalkyl. In some embodiments, $R^3$ is tris(hydroxyC$_{1-6}$alkyl)methyl, and $R^1$ and $R^2$ are hydroxylalkyl. In some embodiments, $R^3$ is tris(hydroxymethyl)methyl. $R^1$ and $R^2$ are hydroxylethyl.

In some embodiments, the organic base is selected from the group consisting of diethanolamine, triethanolamine, tris(hydroxymethyl)aminomethane (Tris), sodium glycine, imidazole, 1-methylimidazole, 2-methylimidazole, and 4(5)-methylimidazole, and 1,2-diaminoethane. In some embodiments, the organic base is tris(hydroxymethyl)aminomethane derivatives.

In some embodiments, the organic base is selected from the group consisting of 2-(bis(2-hydroxyethyl)amino)-2-(hydroxymethyl)propane-1,3-diol, sodium glycine, sodium lysine, sodium histidine, and sodium arginine.

In some embodiments, the mole ratio of artesunate and the organic base is in the range of about 1:0.25 to about 1:15. In some embodiments, the mole ratio of artesunate and the organic base is in the range of about 1:0.5 to about 1:15. In some embodiments, the mole ratio of artesunate and the organic base is in the range of from about 1:1 to about 1:15. In some embodiments, the mole ratio of artesunate and the organic base is in the range of from about 1:1.5 to about 1:11. In some embodiments, the mole ratio of artesunate and the organic base is in the range of about 1:4 to about 1:6. In some embodiments, the mole ratio of artesunate and the organic base is in the range of about 1:1 to about 1:2. In some embodiments, the mole ratio of artesunate and the organic base is about 1:5. In some embodiments, the organic base is imidazole or its derivatives, and the mole ratio of artesunate to imidazole or its derivatives is about 1:1.5 to about 1:2. In some embodiments, the organic base is tris (hydroxymethyl)aminomethane (Tris), or its derivatives, and the mole ratio of artesunate to Tris or its derivatives is about 1:1.5 to about 1:2. In some embodiments, the organic base is triethanolamine or its derivatives, and the mole ratio of artesunate to triethanolamine or its derivatives is about 1:4 to about 1:6.

In some embodiments, the composition comprises artesunate, an organic base and an aqueous solution. The organic base acts as a buffering agent. In some embodiments, artesunate is in the range of about 0.01% to about 20% by weight/volume. In some embodiments, the aqueous solution is sodium chloride solution. In some embodiments, the aqueous solution is normal saline. In some embodiments, the sodium chloride solution is about 0.9% by weight. In some embodiments, the composition further comprises about 5% glucose solution. In some embodiment, the concentration of the organic base is in the range of about 0.1 to about 0.8 M, preferably about 0.2 to about 0.4 M, more preferably about 0.3 to about 0.35 M. The pH of the solution described herein is in the range of about 7.5 to about 9.0, preferably about 8.0 to about 8.5, more preferably about 8.0±0.2.

In some embodiments, the composition comprises artesunate, an organic base and a glucose solution. In some embodiments, the glucose solution is about 5% by weight/volume.

In some embodiments, the composition comprises artesunate and tris(hydroxymethyl)aminomethane in an aqueous solution. In some embodiments, the concentration of tris(hydroxymethyl)aminomethane is in the range of about 0.1 to about 0.8 M mol/L. In some embodiments, the mole ratio of artesunate to tris(hydroxymethyl)aminomethane is in the range of about 1:2 to about 1:15. In some embodiments, the mole ratio of artesunate to tris(hydroxymethyl)aminomethane is in the range of about 1:2 to about 1:12. In some embodiments, the concentration of artesunate is about 10 mg/mL to about 20 mg/L.

In some embodiment, the composition comprises artesunate and tris(hydroxymethyl)aminomethane in an about 0.9% sodium chloride solution. In some embodiments, the concentration of artesunate is about 10 mg/mL to about 20 mg/L.

In some embodiments, the composition comprises artesunate, tris(hydroxymethyl)aminomethane, and phosphoric acid in an aqueous solution. In some embodiments, the composition comprises artesunate, tris(hydroxymethyl)aminomethane, and acetic acid in an aqueous solution. In some embodiments, the concentration of artesunate is about 10 mg/mL to about 20 mg/L. In some embodiments, the composition has a pH in the range of about 7.2 to about 8.0±0.2.

In some embodiments, the composition comprises a buffering agent. In some embodiments, the buffering agent is selected from the group consisting of tris(hydroxymethyl)aminomethane, ammonium, histidine, citrate, succinate, acetate, phosphate, glycine, arginine and lysine.

In some embodiments, the composition further comprises phosphoric acid. In some embodiments, the composition has a pH in a range of from about 7.2 to about 8. In some embodiments, the composition has a pH in a range of from about 7.2 to about 7.8.

In some embodiments, the composition comprises artesunate as a first therapeutic agent, an organic base and a second therapeutic agent. The second therapeutic agent can be any suitable therapeutic agents. In some embodiments, the second therapeutic agent is other antimalarial agents, such as pyronaridine, mefloquine, piperaguine, primaquine, amodiaquine, sulfadoxine-pyrimethanmine, and lumefantrine. In some embodiments, the second therapeuticeand is anticancer agents. Any suitable anticancer agents can be used for therapeutic effects.

Composition II

The present disclosure provides a composition comprising artesunate and an organic base. The organic base is a 5-8 membered ring compound, each of the ring members is independently selected from carbon, nitrogen, oxygen, sulfur, and at least one ring member is nitrogen. The ring contains zero, one, two, or three double bonds. The ring is substituted by k substituents independently selected from $R^{1a}$, k is 0, 1, 2, 3, 4, 5, 6, 7, or 8; and two or more substituents $R^{1a}$ are selected independently from one another.

$R^{1a}$ is selected from the group consisting of hydrogen, halogen, cyano, azido, nitro, SCN, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl; or $R^{1a}$ may combine with an atom or atoms to which it is attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

The present disclosure provides a composition comprising artesunate and an organic base of formula (II):

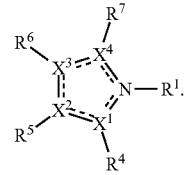

(II)

$X^1$, $X^2$, $X^3$, and $X^4$ is independently selected from the group consisting carbon, nitrogen, oxygen and sulfur. The ring contains zero, one or two double bonds. $R^1$ is selected from the group consisting of absent, hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl. $R^4$, $R^5$, $R^6$, and $R^7$ are independently selected from the group consisting of absent, hydrogen, halogen, cyano, azido, nitro, SCN, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl.

$R^1$ and $R^4$, $R^4$ and $R^5$, $R^5$ and $R^6$, $R^6$ and $R^7$ or $R^1$ and $R^7$ may independently combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, the ring contains two double bonds. In some embodiments, at least three of $X^1$, $X^2$, $X^3$, and $X^4$ are carbon.

In some embodiments, $R^1$ is hydrogen. In some embodiments, $R^1$ is absent.

In some embodiments, at least one of $R^4$, $R^5$, $R^6$, and $R^7$ is $C_{1-6}$ alkyl. In some embodiments, at least one of $R^4$, $R^5$, $R^6$, and $R^7$ is methyl.

In some embodiments, the organic base is of formula (III):

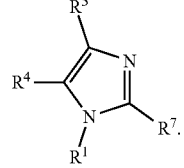

(III)

$R^1$ is selected from the group consisting of hydrogen, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl. $R^4$, $R^5$, and $R^7$ are independently selected from the group consisting of absent, hydrogen, halogen, cyano, azido, nitro, SCN, unsubstituted or substituted alkyl, unsubstituted or substituted alkenyl, unsubstituted or substituted alkynyl, unsubstituted or substituted carbocyclic, unsubstituted or substituted $C_{6-12}$ aryl, unsubstituted or substituted 3-12 membered heterocyclic, and unsubstituted or substituted 5-12 membered heteroaryl.

$R^1$ and $R^4$, $R^4$ and $R^5$, or $R^1$ and $R^7$ may independently combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl.

In some embodiments, $R^1$ is hydrogen.

In some embodiments, at least one of $R^4$, $R^5$, and $R^7$ is alkyl substituted with a member selected from the group consisting of hydroxyl, thiol, carboxyl, carbamoyl, ester, amine, halogen, nitro, and cyano. In some embodiments, at least one of $R^4$, $R^5$, and $R^7$ is $C_{1-20}$ unsubstituted or substituted alkyl. In some embodiments, at least one of $R^4$, $R^5$, and $R^7$ is selected from the group consisting of methyl, ethyl, propyl, cyclopropyl, butyl, cyclobutyl, pentyl, cyclopentyl, hexyl and cyclohexyl. In some embodiments, at least one of $R^4$, $R^5$, and $R^7$ is methyl.

In some embodiments, the organic base is selected from the group consisting of imidazole, 1-methylimidazole, 2-methylimidazole, and 4(5)-methylimidazole.

In some embodiments, the mole ratio of artesunate and the organic base is in the range of about 1:0.25 to about 1:15. In some embodiments, the mole ratio of artesunate and the organic base is in the range of about 1:1 to about 1:15. In some embodiments, the mole ratio of artesunate and the organic base is in the range of about 1:1.5 to about 1:11. In some embodiments, the mole ratio of artesunate and the organic base is in the range of about 1:2 to about 1:6. In some embodiments, the mole ratio of artesunate and the organic base is in the range of about 1:1 to about 1:3. In some embodiments, the base is imidazole or its derivatives, and the mole ratio of artesunate to imidazole or its derivatives is in the range of about 1:1.5 to about 1:2.

In some embodiments, the composition comprises artesunate, an organic base of formula (II) or formula (III), and an aqueous solution. The organic base acts as a buffering agent. In some embodiments, artesunate is the range of about 0.01% to about 20% by weight/volume. In some embodiments, the aqueous solution is sodium chloride solution. In some embodiments, the aqueous solution is normal saline. In some embodiments, the sodium chloride solution is at about 0.9% by weight/volume.

In some embodiments, the composition comprises artesunate, an organic base of formula (II) or formula (III), and a glucose solution. In some embodiments, the glucose solution is about 5% by weight.

In some embodiment, the composition further comprises phosphoric acid. In some embodiment, the composition further comprises acetic acid. In some embodiments, the composition has a pH in the range of about 7.2 to about 7.8, such as 7.8±0.2.

In some embodiment, the concentration of the organic base is in the range of about 0.1 to about 0.8 M, preferably about 0.2 to about 0.4 M, more preferably about 0.3 to about 0.35 M. The pH of the solution described herein is in the range of about 7.5 to about 9.0, preferably about 8.0 to about 8.5, more preferably about 8.0±0.2.

In some embodiments, the composition comprises artesunate as a first therapeutic agent, an organic base and a second therapeutic agent. The second therapeutic agent can be any suitable therapeutic agents. In some embodiments, the second therapeutic agent is other antimalarial agents, such as pyronaridine, mefloquine, piperaguine, primaquine, amodiaquine, sulfadoxine-pyrimethanmine, and lumefantrine. In some embodiments, the second therapeuticeand is anticancer agents. Any suitable anticancer agents can be used for therapeutic effects.

Formulations

The present disclosure provides a formulation of artesunate for parenteral injections. The formulation comprises artesunate, an organic base, and a dissolution medium. The disclosed formulation is suitable for intravenous, intramuscular, intrathecal, intrarectal, intraperitoneal, oral or topical administration.

The dissolution medium can be any suitable medium for injection. In some embodiments, the dissolution medium is an aqueous solution. In some embodiments, the dissolution medium is sodium phosphate buffered solution. In some embodiments, the dissolution medium is a buffering solution containing sodium chloride, phosphate, and glucose. In some embodiments, the dissolution medium contains about 0.9% sodium chloride by weight/volume, about 5% glucose by weight/volume, and sodium phosphate. In some embodiments, the formulation further comprises dextrins, lecithin, mannitol, xylitol, orbital, phosphoric acid or acetic acid.

In some embodiments, the pH of the formulation is in the range of about 7.2 to about 8. In some embodiments, the pH of the formulation is in the range of about 7.2 to about 7.8. The disclosed formulation is suitable for parenteral, such as intramuscular or intramuscular administration.

In some embodiments, the organic base is of formula (I), (II) or (III).

Examples of the bases in the disclosure formulation include: diethanolamine, triethanolamine, 1,2-diaminoethane, tris(hydroxymethyl)aminomethane, 2-(bis(2-hydroxyethyl)amino)-2-(hydroxymethyl)propane-1,3-diol, glycine, lysine, histine, arginine, imidazole, 1-methylimidazole, 2-methylimidazole, and 4(5)-methylimidazole.

In some embodiments, the formulation comprises artesunate, an organic base and an aqueous solution. In some embodiments, the aqueous solution is sodium chloride solution. In some embodiments, the sodium chloride is about 0.9% by weight/volume. In some embodiments, the formulation further comprises about 5% glucose solution. In some embodiments, the concentration of the organic base is in the range of from about 0.1 to about 0.5 M. In some embodiments, the concentration of the organic base is from about 0.2 to about 0.4 M. In some embodiments, the concentration of the organic base is from about 0.3 to about 0.35 M. The pH of the solution described herein is in the range of about 7.5 to about 9.0, preferably about 8.0 to about 8.5, more preferably about 8.0±0.2.

In some embodiments, the formulation comprises artesunate, an organic base and a glucose solution. In some embodiments, the glucose solution is about 5% by weight. In some embodiments, the composition further comprises phosphoric acid. In some embodiments, the composition has a pH in a range of from about 7.2 to about 8. In some embodiments, the composition has a pH in a range of from about 7.2 to about 7.8.

In some embodiments, the formulation comprises artesunate and tris(hydroxymethyl)aminomethane in an aqueous solution. In some embodiment, the composition comprises artesunate and tris(hydroxymethyl)aminomethane in an about 0.9% sodium chloride solution.

In some embodiments, the concentration of tris(hydroxymethyl)aminomethane is in the range of from about 0.1 to about 0.5 M. In some embodiments, the concentration of the tris(hydroxymethyl)aminomethane is from about 0.2 to about 0.4 M. In some embodiments, the concentration of tris(hydroxymethyl)aminomethane is from about 0.3 to about 0.35 M. In some embodiments, the concentration of tris(hydroxymethyl)aminomethane is about 0.03 mol/L, about 0.039 mol/L, or about 0.078 mol/L.

In some embodiments, artesunate is in the range of 0.01% to 20% by weight/volume. In one example, the concentration of artesunate is in the range of about 0.1 to about 2% by weight/volume. In another example, the concentration of artesunate is in the range of about 1 to about 10% by weight/volume. In some embodiments, the concentration of artesunate is about 10 mg/mL. In some embodiments, the mole ratio of artesunate to tris(hydroxymethyl)aminomethane is in the range of about 1:2 to about 1:15. In some embodiments, the mole ratio of artesunate to tris(hydroxymethyl)aminomethane is in the range of about 1:2 to about 1:12.

In some embodiments, the formulation comprises artesunate and tris(hydroxymethyl)aminomethane in a buffering solution. The buffering solution comprises a buffering agent. In some embodiments, the buffering agent is selected from the group consisting of ammonium, histidine, citrate, succinate, acetate, phosphate, glycine, arginine and lysine. The pH of the solution described herein is in the range of about 7.5 to about 9.0, preferably about 8.0 to about 8.5, more preferably about 8.0±0.2.

In some embodiments, the formulation comprises artesunate, tris(hydroxymethyl)aminomethane, and phosphoric acid in an aqueous solution. In some embodiments, the concentration of tris(hydroxymethyl)aminomethane is in the range of from about 0.1 to about 0.8 M. In some embodiments, the concentration of tris(hydroxymethyl)aminomethane is in the range of from about 0.1 to about 0.5 M. In some embodiments, the concentration of the tris(hydroxymethyl) aminomethane is from about 0.2 to about 0.4 M. In some embodiments, the concentration of tris(hydroxymethyl)aminomethane is from about 0.3 to about 0.35 M. In some embodiments, the concentration of tris(hydroxymethyl)aminomethane is about 0.039 mol/L. In some embodiments, the concentration of tris(hydroxymethyl)aminomethane is about 0.078 mol/L.

In some embodiments, the formulation comprises artesunate, tris(hydroxymethyl)aminomethane, and acetic acid in an aqueous solution. In some embodiments, the concentration of tris(hydroxymethyl)aminomethane is in the range of from about 0.1 to about 0.8 M. In some embodiments, the concentration of tris(hydroxymethyl)aminomethane is in the range of from about 0.1 to about 0.5 M. In some embodiments, the concentration of the tris(hydroxymethyl)aminomethane is from about 0.2 to about 0.4 M. In some embodiments, the concentration of tris(hydroxymethyl)aminomethane is from about 0.3 to about 0.35 M. In some embodiments, the concentration of tris(hydroxymethyl)aminomethane is about 0.039 mol/L. In some embodiments, the concentration of tris(hydroxymethyl)aminomethane is about 0.078 mol/L.

In some embodiments, the formulation comprises artesunate at about 10 mg/mL, and tris(hydroxymethyl)aminomethane at about 0.039 mol/L in a phosphoric acid solution. In some embodiments, the formulation comprises artesunate at about 10 mg/mL, and tris(hydroxymethyl) aminomethane at about 0.078 mol/L in a phosphoric acid solution. In some embodiments, the formulation comprises artesunate at about 10 mg/mL, and tris(hydroxymethyl) aminomethane at about 0.3 mol/L in a phosphoric acid solution.

In some embodiments, the formulation comprises artesunate as a first therapeutic agent, an organic base and a second therapeutic agent in an aqueous solution. The second therapeutic agent can be any suitable therapeutic agents. In some embodiments, the second therapeutic agent is other antimalarial agents, such as pyronaridine, mefloquine, piperaguine, primaquine, amodiaquine, sulfadoxine-pyrimethanmine, and lumefantrine. In some embodiments, the second therapeuticeand is anticancer agents. Any suitable anticancer agents can be used for therapeutic effects.

The formulation was prepared prior to use by: providing artesunate; providing a solution comprising an organic base; and adding the solution to artesunate to provide the formulation. For example, the injectable formulation of the present disclosure was prepared by mixing artesunate with an aqueous solution containing a base described herein. Without wishing to be bound by theory, artesunate becomes negatively charged and dissolved. The formulation is freshly prepared immediately before use to minimize instability. In some embodiments, the injectable formulation is prepared by adding a solution of the disclosed bases to artesunate powder. The solution is about 5% glucose, normal saline, or about 5% glucose saline solution. Then the mixture is mixed gently to provide a clear injectable solution.

The methods of the present disclosure dissolve artesunate fast and thoroughly, generating a clear solution for parenteral administration. The methods provide a formulation of artesunate injection suitable for the treatment of malaria and other diseases.

The formulation from present disclosure has many advantages over the current clinically used two-step artesunate/sodium bicarbonate method. The bases of the present disclosure are organic compounds and the dissolution of artesunate in an aqueous phase does not produce carbon dioxide bubbles, as in the case where 5% sodium bicarbonate is used. Further, while the artesunate/sodium bicarbonate method involves two steps, dissolution and dilution, the preparation from the present disclosure is a single step dissolution—adding the aqueous base solution to artesunate powder and swirling gently to generate the desired injectable solution. The formulation of the present disclosure is very convenient to prepare. The resulting clear injectable solution shows no fizzing and sustained cloudiness, which is generally observed in the sodium carbonate formulation. In a comparative experiment, the inventors observed that the time needed to dissolve 10 mg of artesunate in 1 mL of imidazole saline solution (0.039 M) was two to three minutes, while it took five to seven minutes with 5% sodium bicarbonate solution.

In addition, the stability of artesunate in the formulation of the present disclosure was enhanced in comparison with the artesunate/sodium bicarbonate method. At room temperature, the artesunate formulation of the present disclosure starts to become cloudy and precipitate out after five to seven hours, while the cloudiness and precipitation occurs within two to three hours in the formulation of artesunate/sodium bicarbonate. The cloudiness or precipitation has been used as an indication in the clinic to discard the injection solution. The precipitate from the formulations had been identified mainly as dihydroartemisinin, an active antimalarial agent. The improved formulation stability may extend the time window for the injectable formulation application. This may imply a possibility to administer artesunate by intravenous infusion, which may improve therapeutic efficacy of artesunate by overcoming the drawback of its short plasma half-life (about 20 minutes, Zaloumis el al, CPT Pharmacometrics & Syst Pharmacol, 2014, 5; 3:e145). Moreover, when the formulation from the present disclosure was diluted from 10 mg/mL to 1 mg/mL, or to 0.1 mg/mL, no precipitation was observed within 12 hours, indicating that the present formulation may be suitable for intravenous infusion for several hours to maintain a steady concentration of artesunate in the plasma. In addition, the formulation of the present disclosure may be made without sodium salt, favorable for patients who need to avoid the salts. The formulation of the present disclosure may also be prepared by dissolving artesunate powder with commercially available THAM solution [tris(hydroxymethyl)aminomethane acetate buffer solutions, 0.3 M] to treat patients with acidosis conditions (such as in acute lung injury).

The other desirable feature is that the pH of the formulation (7.2-7.6) is ideal for intramuscular or intravenous injection. In contrast, the pH of the artesunate/sodium bicarbonate formulation is about 7.9-8.0. For instance, the pH of 10 mg/mL artesunate in imidazole normal saline is 7.4±0.2 (mole ratio 1:1.5/artesunate:imidazole).

The preferred organic bases from the present disclosure are pharmaceutically acceptable and have been applied in injectable formulations. For instance, imidazole has been used in the parenteral formulations of selezen (imidazole salicylate), and tris(hydroxymethyl)aminomethane in Zybrestat (Fosbretabulin tris(hydroxymethyl)aminomethane) for intravenous injection and in Hemabate (carboprost tromethamine) for parenteral administration.

The formulation of artesunate from the present disclosure can be administered by intramuscular or intravenous injection, and by oral or topical administration. The concentration of artesunate in the formulation may be in the range of about 0.01 to about 20% by weight/volume. In one example, the concentration is in the range of about 0.1 to about 2% by weight/volume. In another example, the concentration is in the range of about 1 to about 10% by weight/volume. The desired concentration for use can be determined by people skilled in the art. The effective dosage may be affected by age, body weight or diseases to be treated, and can be selected by people skilled in the art. For example, in the treatment of malaria, a common unit dosage for manufacture is 60 mg or 110 mg and a typical dose for injection is 2.4 mg/kg body weight with 10 mg/mL, once daily intravenous injection for 5-7 days for a course, with doubled dose for the first administration and the total doses are 360-480 mg for adults (instructed by Guilin Pharmaceuticals, Guangxi, China).

Methods of Treatment

A method for treating diseases or disorders associated with parasite infections comprises administrating a pharmaceutically effective amount of the disclosed composition or the formulation to a subject. In some instance, the parasite infection is selected from the group consisting of malaria, schistosoma japonicum and toxoplasma infections. In some examples, the malarial infection is caused by severe *Plasmodium falciparum* malara.

Further, the formulation of artesunate from the present disclosure can be used to treat many other diseases beyond malaria, including prevention and treatment of schistosoma japonicum, antitoxoplasma infection, anticancer and antivirus, treatment of inflammatory and immune dysfunctions (e.g. rheumatoid arthritis, nephrotic syndrome, and lupus nephritis), pancreatitis and birth control.

The artesunate formulation according to the present disclosure may be administered in combination with other therapeutic agents to enhance treatment efficiency. For example, the formulation from the invention may be combined with other anti-malarial drugs to treat malarial patients (e.g. pyronaridine, amodiaquine, or sulfadoxine-pyrimethamine, Bukirwa et al, Cochrane Database Syst Rev, 2014, Mar. 4; Angus B, Expert Rev Clin Pharmacol, 2014, 7(3): 299-316), or with anticancer agents to treat cancer patients (e.g. vinorelbine and cisplatin, Zhang et al, J Chin Integr Med, 2008, 6:134).

In some embodiments, the pharmaceutically effective amount of artesunate administered to a patient is about 0.2-10 mg/kg body weight once or twice per day for about 2 to 30 days.

In some embodiments, the disclosed composition or formulation is for use in the treatment of cancers, organ injury, inflammatory disorders, heart diseases, sepsis, stroke, burns injury, virus infections, diabetes, liver diseases and lung disorders. In some embodiments, the cancer is selected from the group consisting of leukemia, colorectal cancer, brain/CNS cancer, bladder cancer, breast cancer, ovarian cancer, lung cancer, melanoma, oral cavity and oropharyngeal cancer, pancreatic cancer and bone cancer. In some embodiments, the heart disease is selected from the group consisting of cardiac hypertrophy, heart failure, myocardial infarct and coronary heart disease. In some embodiments, the organ injury is induced by malaria, burns, sepsis and lupus. In some embodiments, the organ injury is selected from a group consisting of renal injury, lung injury, liver injury, head injury and intestinal injury. In some embodiments, the kidney disease is selected from the group consisting of acute kidney, chronic kidney, kidney failure and uremia. In some embodiments, the inflammatory disease is selected from the group consisting of rheumatoid arthritis, nephrotic syndrome, and lupus nephritis.

In some embodiments, the organ injury is induced by haemorrhage. The organ injury is selected from the group consisting of trauma injury, pancreatitis injury, intestinal injury, brain and head injury, lung injury, spinal cord injury and respiratory distress syndrome.

In some embodiments, the diabetes is type I diabetes.

In some embodiments, the liver disease is hepatic fibrosis.

In some embodiments, the lung disease is selected from the group consisting of asthma, respiratory distress syndrome or idiopathic pulmonary fibrosis.

In some embodiments, a method of treating ischemia-reperfusion in a surgery comprises administrating to a subject a pharmaceutically effective amount of the disclosed composition or formulation. In some embodiments, the surgery is selected from the group consisting of kidney transplantation, kidney and pancreas transplantation, and coronary artery bypass graft.

Kits

The present disclosure provides a kit to prepare a single dosage of artesunate formulation. The kit comprises:
1. Vial A containing a pharmaceutically effective amount of artesunate; and
2. Vial B containing a pharmaceutically acceptable injection solution of an organic base.

Prior to use, the solution in vial B was added to vial A with mixing to complete dissolution. A medical syringe was used to add the solution from vial B to vial A. Then, the formulated solution was taken using the same syringe for parenteral injection.

Alternatively, Vial B may contain the organic base in a pure solid or liquid form. The organic base was dissolved in a suitable dissolution medium before adding to artesunate powder.

The artesunate was in a form of powder. The artesunate powder in vial A and the base solution in vial B were pharmaceutically manufactured, sterilized and packaged for clinical applications.

The unit dosage of artesunate in vial A may be about 60 mg to about 110 mg, or determined by the required dosage for treatments. In some examples, vial A contains 60 mg of artesunate powder, and vial B contains 6 mL of an organic base in 5% glucose solution, normal saline, or any suitable buffering solutions.

It was found that the use of artesunate dry powder can minimize the degradation, and the formulation according to the disclosure can be conveniently prepared immediately before injection.

The following examples are illustrative, but not limiting, of the method and composition of the present disclosure.

EXAMPLES

Example 1. Triethanolamine Normal Saline Solution (0.13 M)

To normal saline (0.9% NaCl) was added triethanolamine (1.94 g, 13 mmol) with stirring and the final volume was adjusted to 100 mL to produce 0.13 M triethanolamine normal saline solution.

Example 2. Imidazole Normal Saline Solution (0.039 M)

To normal saline (about 0.9% NaCl) was added imidazole (0.265 g, 3.9 mmol) with stirring and the final volume was adjusted to 100 mL to yield 0.039 M imidazole normal saline solution.

Example 3. 2-Methylimidazole Normal Saline Solution (0.039 M)

To normal saline (0.9% NaCl) was added 2-methylimidazole (0.32 g, 3.9 mmol) with stirring and the final volume was adjusted to 100 mL to yield 0.039 M 2-methylmidazole normal saline solution.

Example 4. Imidazole Normal Saline Solution (0.052 M)

To normal saline (0.9% NaCl) was added imidazole (0.354 g, 5.2 mmol) with stirring and the final volume as adjusted to 100 mL to yield 0.052 M imidazole normal saline solution.

Example 5. Triethanolamine Artesunate Normal Saline Formulation (10 mg/mL)

To artesunate powder (60 mg, 0.156 mmol) was added 0.13 M triethanolamine normal saline solution from Example 1 (6 mL, 0.78 mmol) and the mixture was gently swirled for 2-3 minutes to yield a clear solution of triethanolamine artesunate. $^1$HNMR ($D_2O$, 360 MHz) δ5.66-5.69 (10-H), 5.59 (12a-H), 3.65 (t, triethanolamine, $CH_2CH_2OH$, 2H), 2.80 (t, triethanolamine, $CH_2CH_2OH$, 2H), 2.38-2.42 (15-H), 2.17-2.24(14-H), 1.31(3-$CH_3$), 0.84-0.86 (6-$CH_3$), 0.77-0.79 (9-$CH_3$).

Example 6. Imidazole Artesunate Normal Saline Formulation (10 mg/mL)

To artesunate powder (60 mg, 0.156 mmol) was added 0.039 M imidazole solution normal saline from Example 2 (6 mL, 0.234 mmol) and the mixture was gently swirled for 2-3 minutes to give a clear solution of imidazole artesunate. $^1$HNMR ($D_2O$, 360 MHz) δ7.27 (s, imidazole, 2H), 5.65-5.68 (10-H), 5.58 (12a-H), 2.40-2.42 (15-H), 2.17-2.24 (14-H), 1.30 (3-$CH_3$), 0.83-0.85 (6-$CH_3$), 0.76-0.78 (9-$CH_3$), pH 7.4±0.2.

Example 7. Imidazole Artesunate Normal Saline Formulation (10 mg/mL)

To artesunate powder (60 mg, 0.156 mmol) was added 0.052 M imidazole normal saline solution from Example 4 (6 mL, 0.312 mmol) and the mixture was gently swirled for 2-3 minutes to give a clear solution of imidazole artesunate.

Example 8. 2-Methylimidazole Artesunate Normal Saline Formulation (10 mg/mL)

To artesunate powder (60 mg, 0.156 mmol) was added 0.039 M 2-methylimidazole normal saline solution from Example 3 (6 mL, 0.234 mmol) and the mixture was gently swirled for 2-3 minutes to give a clear solution of 2-methylimidazole artesunate. $^1$HNMR ($D_2O$, 360 MHz) δ7.08 (s, 2-methylimidazole, 2H), 5.65-5.68 (10-H), 5.58 (12a-H), 2.41(s, 2-methylimidazole, $CH_3$), 2.38-2.42 (15-H), 2.16-2.23 (14-H), 1.30 (3-$CH_3$), 0.83-0.85 (6-$CH_3$), 0.76-0.78 (9-$CH_3$), pH 7.4±0.2, pH 7.4±0.2.

Example 9. Tris(Hydroxymethyl)Aminomethane Normal Saline Solution (0.039 M)

To normal saline (0.9% NaCl) was added tris(hydroxymethyl)aminomethane (0.47 g, 3.9 mmol) with stirring and the final volume was adjusted to 100 mL to yield 0.039 M tris(hydroxymethyl)aminomethane normal saline solution.

Example 10. Tris(Hydroxymethyl)Aminomethane Artesunate Normal Saline Formulation (10 mg/mL)

To artesunate powder (60 mg, 0.156 mmol) was added 0.039 M tris(hydroxymethyl)aminomethane normal saline solution from Example 9 (6 mL, 0.234 mmol) and the mixture was gently swirled for 2-3 minutes to provide a clear solution of tris(hydroxymethyl)aminomethane artesunate. $^1$HNMR ($D_2O$, 360 MHz) δ5.66-5.69 (10-H), 5.59 (12a-H), 3.57 (s, tris(hydroxymethyl)aminomethane), 2.38-2.42 (15-H), 2.17-2.24 (14-H), 1.30 (3-$CH_3$), 0.84-0.86 (6-$CH_3$), 0.77-0.79 (9-$CH_3$).

Example 11. Tris(Hydroxymethyl)Aminomethane Normal Saline Solution (0.078 M)

To normal saline (0.9% NaCl) was added tris(hydroxymethyl)aminomethane (0.94 g, 7.9 mmol) with stirring and the final volume was adjusted to 100 mL to yield 0.078 M tris(hydroxymethyl)aminomethane normal saline solution.

Example 12. Tris(Hydroxymethyl)Aminomethane Artesunate Normal Saline Formulation (10 mg/mL)

To artesunate powder (60 mg, 0.156 mmol) was added 6 mL of 0.078 M tris(hydroxymethyl)aminomethane solution from Example 11 (6 mL, 0.468 mmol) and the mixture was gently swirled for 2-3 minutes to provide a clear normal saline solution of tris(hydroxymethyl)aminomethane artesunate, pH 7.4±0.2.

Example 13. Tris(Hydroxymethyl)Aminomethane Acetate Buffered Solution (0.3 M)

To deionized water was added tris(hydroxymethyl)aminomethane (3.6 g, 30 mmol) and the solution was adjusted to pH 8 with acetic acid, with the final volume 100 mL, to yield 0.3 M tris(hydroxymethyl)aminomethane acetate buffered solution.

Example 14. Artesunate in Tris(Hydroxymethyl)Aminomethane Acetate Buffered Solution (10 mg/mL)

To artesunate powder (60 mg, 0.156 mmol) was added 6 mL of the tris(hydroxymethyl)aminomethane acetate buffered solution from Example 13 (0.3 M, 1.8 mm) and the mixture was gently swirled for 2-3 minutes to provide a clear artesunate solution in tris(hydroxymethyl)aminomethane acetate buffer, pH 7.5±0.2.

Example 15. Tris(Hydroxymethyl)Aminomethane Phosphate Buffered Solution (0.3 M)

To deionized water was added tris(hydroxymethyl)aminomethane (1.82 g, 15 mmol) and the solution was adjusted to pH 8 with 5% phosphoric acid, with the final volume 50 mL, to yield 0.3 M tris(hydroxymethyl)aminomethane phosphate buffered solution.

Example 16. Artesunate in Tris(Hydroxymethyl)Aminomethane Phosphate Buffered Solution (10 mg/mL)

To artesunate powder (60 mg, 0.156 mmol) was added 6 mL of the tris(hydroxymethyl)aminomethane phosphate buffered solution from Example 15 (0.3 M, 1.8 mmol) and the mixture was gently swirled for 2 to 3 minutes to provide a clear artesunate solution in tris(hydroxymethyl)aminomethane phosphate buffer, pH 7.5±0.2.

Example 17. Tris(Hydroxymethyl)Aminomethane Acetate Buffered Solution (0.3 M)

To deionized water was added tris(hydroxymethyl)aminomethane (3.6 g, 30 mmol) and the solution was adjusted to pH 8.6 (8.4-8.7) with acetic acid, adjusted with deionized water to the final volume 100 mL, to yield 0.3 M tris(hydroxymethyl)aminomethane acetate buffered solution.

Example 18. Artesunate in Tris(Hydroxymethyl)Aminomethane Acetate Buffered Solution (10 mg/mL)

To artesunate powder (60 mg, 0.156 mmol) was added 6 mL of the tris(hydroxymethyl)aminomethane acetate buffered solution from Example 17 (0.3 M, 1.8 mmol) and the mixture was gently swirled for 1-2 minutes to provide a clear artesunate solution in tris(hydroxymethyl)aminomethane acetate buffer.

The invention claimed is:

1. A composition comprising artesunate dissolved in an organic base buffer solution, wherein the organic base has formula (I)

wherein $R^1$ and $R^2$ are H, and $R^3$ is tris(hydroxyl$C_{1-2}$alkyl)$C_{1-2}$alkyl and
wherein the concentration of said organic base is in the range of about 0.1 to about 0.5 mol/L and the composition has a pH in the range of about 7.2 to about 8.2.

2. The composition of claim 1, wherein $R^3$ is tris(hydroxymethyl)methyl.

3. A composition comprising artesunate dissolved in an organic base buffer solution, wherein the organic base is tris(hydroxymethyl)aminomethane; and wherein the concentration of tris(hydroxymethyl)aminomethane is in the range of about 0.1 to about 0.5 mol/L and the composition has a pH in the range of about 7.2 to about 8.2.

4. The composition of claim 3, wherein the buffering agent is selected from phosphoric acid, acetic acid, citric acid, succinic acid, glycine, hydrochloric acid, and sulfuric acid, and mixtures thereof.

5. The composition of claim 3, wherein the concentration of artesunate is in the range of about 0.01% to about 20% by weight/volume.

6. The composition of claim 3, wherein the concentration of artesunate is in the range of about 0.1% to about 2% by weight/volume.

7. The composition of claim 3, wherein the composition has a pH about 7.5.

8. The composition of claim 3, wherein the concentration of tris(hydroxymethyl)aminomethane is in the range of about 0.2 to about 0.4 mol/L.

9. The composition of claim 3, wherein the concentration of tris(hydroxymethyl)aminomethane is about 0.1 mol/L.

* * * * *